United States Patent
Kain (10) Patent No.: US 7,017,404 B1
(45) Date of Patent: Mar. 28, 2006

(54) WIRELESS SYSTEM FOR MEASURING PRESSURE AND FLOW IN TUBES

(76) Inventor: Aron Zev Kain, 1 Jodi Ct., Wesley Hills, NY (US) 10952

( * ) Notice: Subject to any disclaimer, the term of this patent is extended or adjusted under 35 U.S.C. 154(b) by 0 days.

(21) Appl. No.: 10/530,066

(22) PCT Filed: Oct. 2, 2003

(86) PCT No.: PCT/US03/31326

§ 371 (c)(1),
(2), (4) Date: Jul. 13, 2005

(87) PCT Pub. No.: WO2004/031709

PCT Pub. Date: Apr. 15, 2004

Related U.S. Application Data (60) Provisional application No. 60/415,373, filed on Oct. 2, 2002.

(51) Int. Cl.
*B60C 23/02* (2006.01)

(52) U.S. Cl. .................................... 73/146.5
(58) Field of Classification Search ............... 73/146, 73/146.5, 715–728, 753
See application file for complete search history.

(56) References Cited

U.S. PATENT DOCUMENTS

| | | | | |
|---|---|---|---|---|
| 4,072,926 A | * | 2/1978 | Shimahara et al. | 340/448 |
| 4,206,762 A | * | 6/1980 | Cosman | 600/438 |
| 4,281,667 A | * | 8/1981 | Cosman | 600/561 |
| 4,653,508 A | * | 3/1987 | Cosman | 600/561 |
| 4,660,568 A | * | 4/1987 | Cosman | 600/561 |
| 5,904,708 A | | 5/1999 | Goedeke | |
| 6,346,886 B1 | | 2/2002 | De La Huerga | |
| 6,924,688 B1 | * | 8/2005 | Beigel | 327/330 |

* cited by examiner

*Primary Examiner*—William Oen
(74) *Attorney, Agent, or Firm*—Katten Muchin Rosenmann LLP (57) ABSTRACT

A remote sensor (100) is remotely placed within a vessel containing a fluid in order to sense a pressure generated by the fluid. The sensor includes an antenna (10) for capturing an externally-generated interrogation signal and for transmitting a response signal, a response circuit (20, 30) coupled to the antenna (10) for receiving the interrogation signal and for generating the response signal, and a sensor element (40) coupled to the response circuit. One or more electrical characteristics of the response circuit (20, 30) change in relation to the sensed pressure, thereby determining measurable characteristics of the response signal. Importantly, the response circuit (20, 30) operates to delay the transmission of the response signal to a time separated from and following transmission of artifacts of the interrogation signal.

23 Claims, 12 Drawing Sheets

WIRELESS SYSTEM FOR MEASURING PRESSURE AND FLOW IN TUBES

This application is the National Stage of International Application No. PCT/US2003/031326, filed Oct. 2, 2003, which claims the benefit under 35 U.S.C. 119 (a–e) of U.S. Provisional Application 60/415,373 filed Oct. 2, 2002, which is herein incorporated by reference.

FIELD OF THE INVENTION

The present invention relates to a system for measuring of the pressure and/or flow of a substance in a tube. More particularly, the present invention relates to a wireless system including an intra-corporeal, externally-powered sensor for measuring of the pressure and/or flow of a substance in a tube.

BACKGROUND OF THE INVENTION

In International Application No. PCT/US02/09543 entitled "Wireless System for Measuring Distension in Flexible Tubes" to Kain ("Kain I"), which is hereby incorporated by reference, methods for measuring blood parameters in living beings are described. As is disclosed in Kain I, it is known in the prior art to measure blood pressure by the implantation of a miniaturized sensor via catheterization. As catheterization in humans ideally requires that the overall diameter of an implanted sensor be 2 millimeters (mm) or less, self-powered sensors that contain internal batteries are not practical at the present time. Hence, other means for supplying energy to the sensor such as energy scavenging by the sensor or external power means are required in order for the sensor to function and meet the size constraints required by the catheterization procedure.

Kain I discloses a pressure sensor including a resonant circuit externally powered and interrogated by radio frequency identification (RFID) techniques to provide a response signal that can be correlated to an implied blood pressure within a blood vessel. However, such response signals may be deleteriously affected by interrogation signals generating signal artifacts including reflections from a variety of sources and other unwanted signal responses.

SUMMARY OF THE INVENTION

The deficiencies of the prior art may be largely overcome by an externally-powered transducer that may be remotely positioned in a fluid within a vessel (for example, a blood vessel) for sensing a pressure generated by the fluid in the vessel. The transducer comprises an antenna for capturing an externally-generated interrogation signal and for transmitting a response signal, a response circuit coupled with the antenna for receiving the interrogation signal and generating the response signal in response to the interrogation signal, and a sensor coupled to the response circuit. The sensor operates to sense a pressure generated by the fluid in the vessel, and adjusts an electrical characteristic of the response circuit in relation to the sensed pressure. Importantly, the response circuit operates to delay the transmission of the response signal to a time separated from and following transmission of artifacts of the interrogation signal. The response circuit may preferably include means for generating acoustic signals as a means for generating the required signal delays.

In an application of the present invention directed to measuring venal or arterial blood pressure, the antenna comprises a shape memory alloy, is insertable into a vein or artery, and changes shape in response to a characteristic of the blood (temperature) in the vein or artery in order to become affixed to an inner wall of the vein or artery.

In a venal blood pressure application, the sensor preferably includes pressure amplification means comprising a lumen containing an incompressible fluid in a sealed lumen tube. A portion of the lumen tube has a deflecting diaphragm coupled to a deflecting spring member which operates with the sensor to affect an electrical characteristic of the response circuit. The deflecting diaphragm is more compliant and undergoes a larger deflection than the lumen tube in response to the generated pressure. The deflection of the deflecting diaphragm as compared to the deflection of the lumen tube is proportional to a ratio of a surface area of the lumen tube to the surface area of the deflecting diaphragm.

BRIEF DESCRIPTION OF THE DRAWING

A more complete understanding of the invention may be obtained by reading the following description of specific illustrative embodiments of the invention in conjunction with the appended drawing in which:

FIG. 15 shows resonant frequency response as a function of conductor plate height above the inductor for the layout of FIG. 14a.

DETAILED DESCRIPTION OF THE PREFERRED EMBODIMENTS

The following detailed description includes a description of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention.

The present invention comprises a wireless system for measuring pressure and/or flow of a substance in a tube. The tube may include biological materials such as blood vessels, as well as industrial materials such as PVC (polyvinyl chloride) or stainless steel. The construction, geometry, and topology of the tube are inconsequential to the workings of the invention, the only tube requirement dictated by the system is that electromagnetic radiation can be introduced through the tube into the sensor component of the system. The cause of the force or pressure as well as the medium through which the force is transmitted to the sensor (gas, liquid or solid) is also inconsequential to the system operation.

This system may be applied to a broad range of applications for measuring pressure and/or flow of a substance in a tube, including, for example, the measurement of the internal blood pressure of an artery or vein, and the checking the ovality of steel pipes as they are buried in the ground for utility services.

The present invention provides a means of externally powering an intra-corporeal transducer (i.e., a transducer positioned within the tube). A key component of the invention couples time diversity techniques with the tube sensor topologies (for example, as taught in Kain I).

Time diversity techniques that allow a delay between the incoming and outgoing signal of interest are well known in the literature. Embodiments of the present invention are described herein that employ two types of devices that allow for time diversity, the Surface Acoustic Wave (SAW) delay line and the SAW bandpass filter. Other devices that provide a significant time delay, for example, such as Bulk Acoustic Wave (BAW) devices and Thickness Shear Mode (TSM) resonators, can also be employed, and are fully contemplated by the present invention. A variety of acoustic signal propogation modes that generate delays such as bulk, horizontal shear, thin rod, and plate modes may be used.

Generally, acoustic structures allow for a much longer time delay (for example, microseconds) than can be achieved with electromagnetic delays (for example, picoseconds) for the same physical distance between two points. Exploiting such long relative delays allow current state of the art electronics to "gate" out undesired replies, multi-path issues, and general environmental interactions with the transmitted electromagnetic wave. The significance of this effect to the present invention will be describer further herein.

Figure 1:
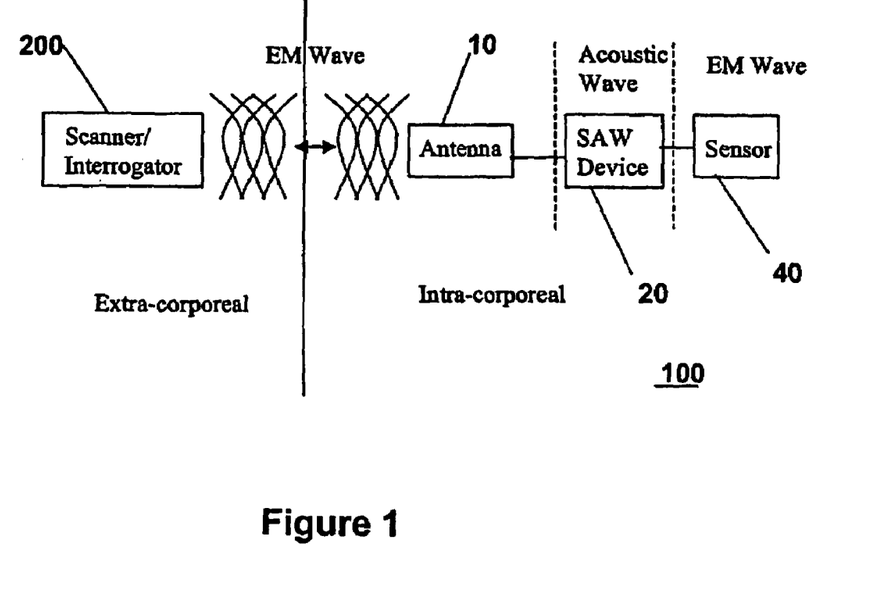
FIG. 1 provides a schematic diagram illustrating the fundamental components in a system according to the present invention.

The schematic diagram illustrating the fundamental components in a system according to the principles of the present invention is shown in FIG. 1. The system comprises an extra-corporeal scanner 200, which communicates with an intra-corporeal transducer 100.

Scanner 200, which is located outside the human body or tube, generates an interrogation signal to be transmitted to transducer 100. Suitable scanners are well known in the art (for example, as are being used currently for RFID systems or remote utility meter reading systems).

The interrogation signal may be an electromagnetic (EM) pulse of some finite duration in nature, and can be of any arbitrary frequency and power level, so long as the implanted device can receive the incoming signal from the externally-positioned scanner through the tube. The frequency/power chosen should be such that penetration of the body or tube is readily achieved. As a specific example, a frequency of 400 MHz is adequate to penetrate deep into the body cavity so that implanted heart monitors can be used. As illustrated in FIG. 1, the antenna 10 of the transponder 100 then detects the EM signal and passes it to the SAW device 20.

The SAW device 20 converts the EM signal into a mechanical vibration (acoustic surface wave). The velocity of the signal in the SAW device, which may be made for example of Quartz or lithium niobate (LiNiO3), is five orders of magnitude slower than in air, so that a substantial delay (for example, less than 1 microsecond (μs) may be achieved even in as little as 3 millimeters (mm) of distance. The mechanical vibration wave travels from one end of the SAW device 20 to the other where it is converted back into an electrical signal, albeit delayed. The electrical signal then interacts with the sensor 40, is reflected back through the chain undergoing a second delay, and returns to the scanner 200 as an electromagnetic (EM) signal, delayed by the round trip time of the SAW device 20 (in our example, by 2 μs). A 2 μs delay corresponds to a frequency of 500 Kilohertz (KHz). Hence, any electronic circuitry that is able to operate at a frequency higher than 500 KHz will be able to discriminate the difference between the outgoing and return signal reply. Clearly, many conventional circuits today operate at frequencies well above 100 Megahertz (MHz).

Figure 1A:
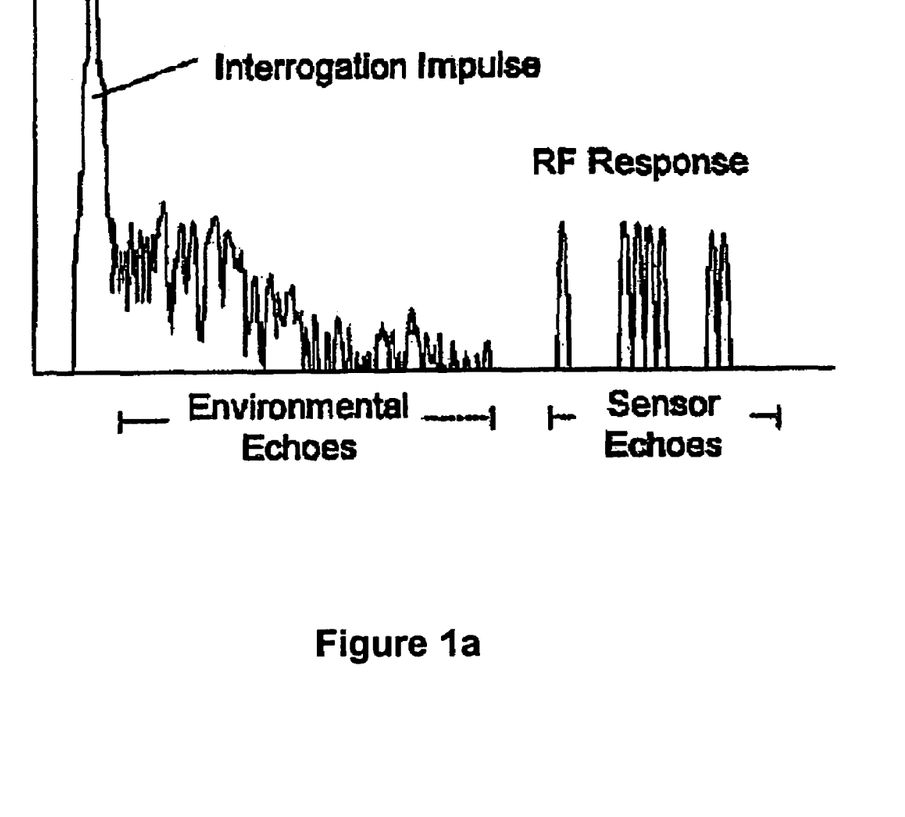
FIG. 1a illustrates the effect of time diversity in distinguishing a signal response consistent with principles of the present invention.

Notice that by using time diversity two things are accomplished. First, electromagnetic (EM) issues such as reflections (for example, objects in the room, multi-path, other body parts, and the like) may be distinguished from sensor signal responses. EM reflections are relatively instantaneous, for example, on the order of less than 10 picoseconds (ps), while the signal of interest may not return from the SAW device 20, for example, for 2 us. This relationship is illustrated in FIG. 1a. In addition, because of the delay, the sensor 40 can remain a completely passive device, powered by the interrogation signal of scanner 200 and therby requiring no internal energy. Even if the such power means generates a return sensor signal diminished by 60 dB from the original interrogation signal, it will be the only signal present after the 2 μs delay. As long as the return sensor signal is above the noise floor of the receiver as determined by an arbitrary signal to noise ratio (SNR), it should be readily detected without concern for EM effects.

Figure 2:
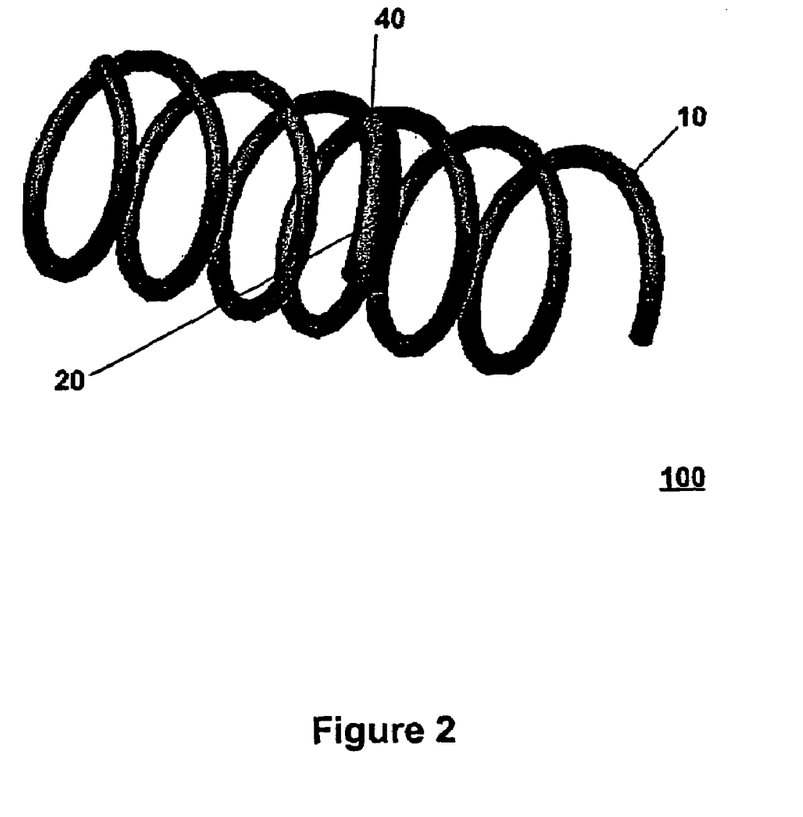
FIG. 2 illustrates a catheter-based transducer according to the principles of the present invention.

FIG. 2 illustrates a catheter-based implanted transducer according to the principles of the present invention. The antenna structure 10 may preferably be made out of shape memory alloys, such that the entire sensor and antenna can be initially introduced into a blood vessel as a straight device, for example, having a diameter less than 2 mm. As the blood warms the shape memory alloy (for example, NiTinol), the warmth causes the antenna 10 to curl into a coil that secures the structure to the inner walls of the blood vessel.

Figure 3:
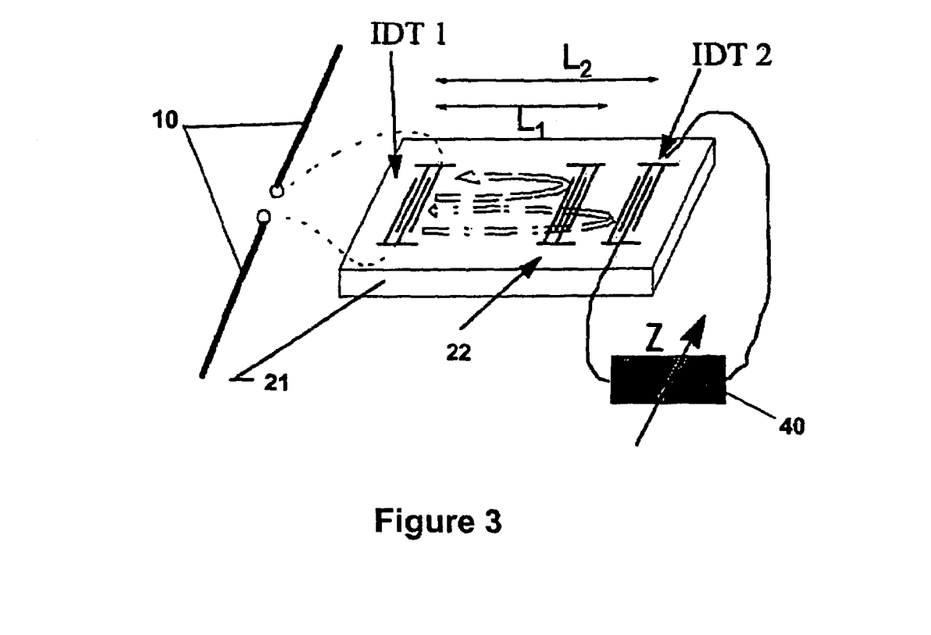
FIG. 3 provides a schematic diagram illustrating the intra-corporeal transducer of FIG. 1.

FIG. 3 provides illustrates the intra-corporeal transducer 100 of FIG. 1 in greater detail, and in particular, illustrates the SAW device 20. The literature is replete with sensors that use SAW delay lines similar to the SAW device of FIG. 3. Interdigital transducer 1 (IDT1) converts the EM signal received by the antenna 10 into a surface acoustic wave which travels along the length of the crystal 21. When the wave impinges on the reference reflector 22, it is reflected back to IDT 1 which converts it to an EM wave, and is then re-radiated by the antenna 10. The length L1 directly determines the delay time between the received (incoming) signal and the re-radiated signal. This signal, for illustration sake, is received by the scanner after 1 µs. It is used as a reference marker (for example, with respect to amplitude and phase) since it has not been effected by any external factor other than the pure delay. This reflection scenario holds true for IDT 2, however the amplitude and phase of the reflected signal are also influenced by the sensor 40 attached IDT 2. As the impedance of the sensor 40 changes, the reflection characteristics of IDT 2 also change. Hence, the reflected amplitude and phase may be directly controlled by the external sensor. A typical sensor used in the prior art is a strain gage, which of course is an impedance (resistance) changing device. Preferably, using the sensors taught by Kain I, the entire delay line and external sensor can be integrated into a single substrate device, as is further illustrated herein. An example layout of such a device is shown in FIGS. 4, 6, and 7.

Figure 4:
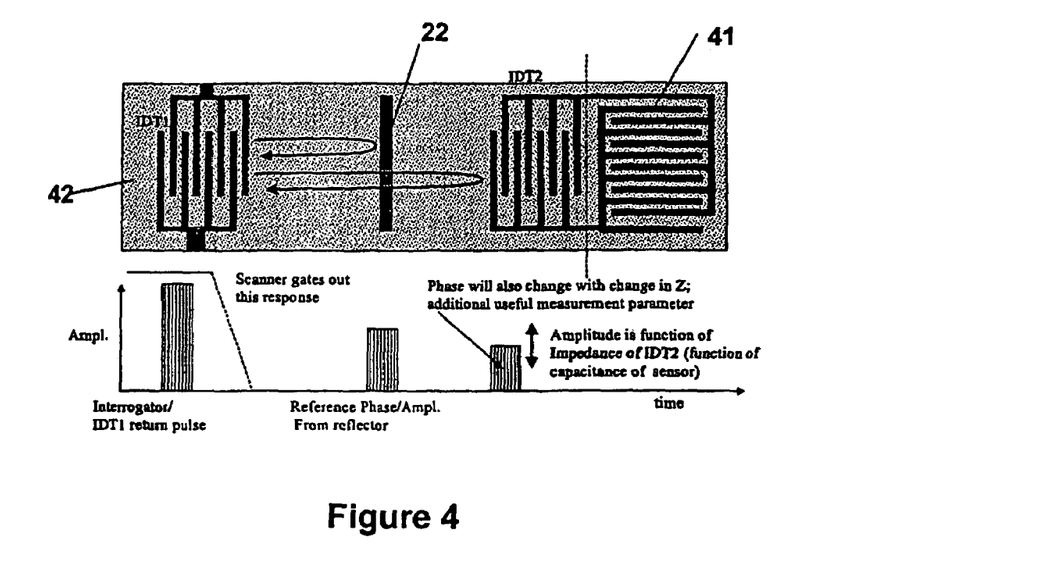
FIG. 4 provides a schematic diagram consistent with the diagram of FIG. 3 illustrating an integrated substrate including a SAW device and an interdigitated capacitor sensor.

As illustrated in FIG. 4, for example, an interdigitated capacitance sensor 41 is directly fabricated on the overall delay line substrate 42, and changes its impedance in relation to the position to a deflecting spring member 43 (shown in FIG. 5) that is placed above it. Operation of a sensor of this type is further described in U.S. Pat. No. 5,546,806 to Kain ("Kain II"). It should be noted that many types of conventional deflecting spring members may be used for adjusting the impedance of the sensor 41, including the folded spring illustrated in FIG. 5.

Figure 6:
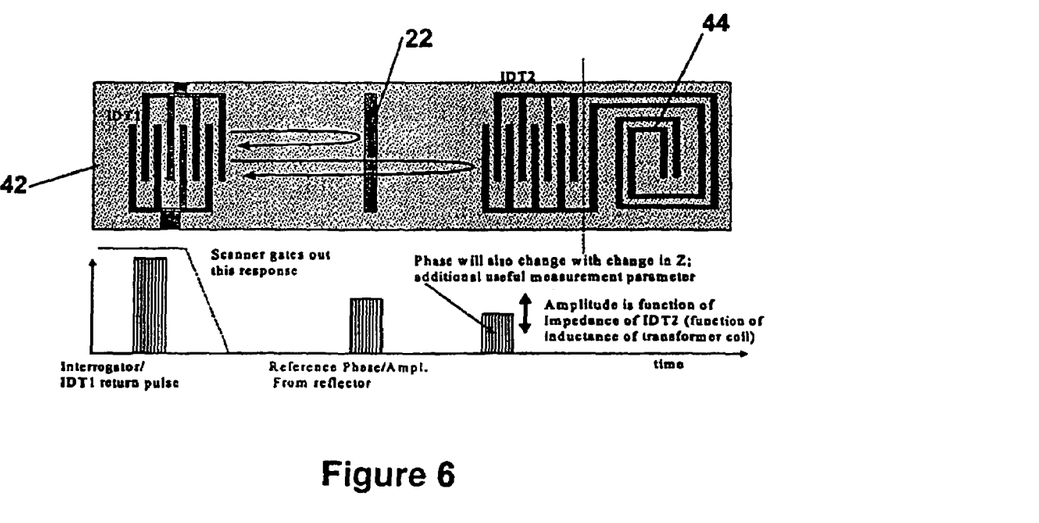
FIG. 6 provides a schematic diagram consistent with the diagram of FIG. 3 illustrating an integrated substrate including a SAW device and a coil sensor.
Figure 7:
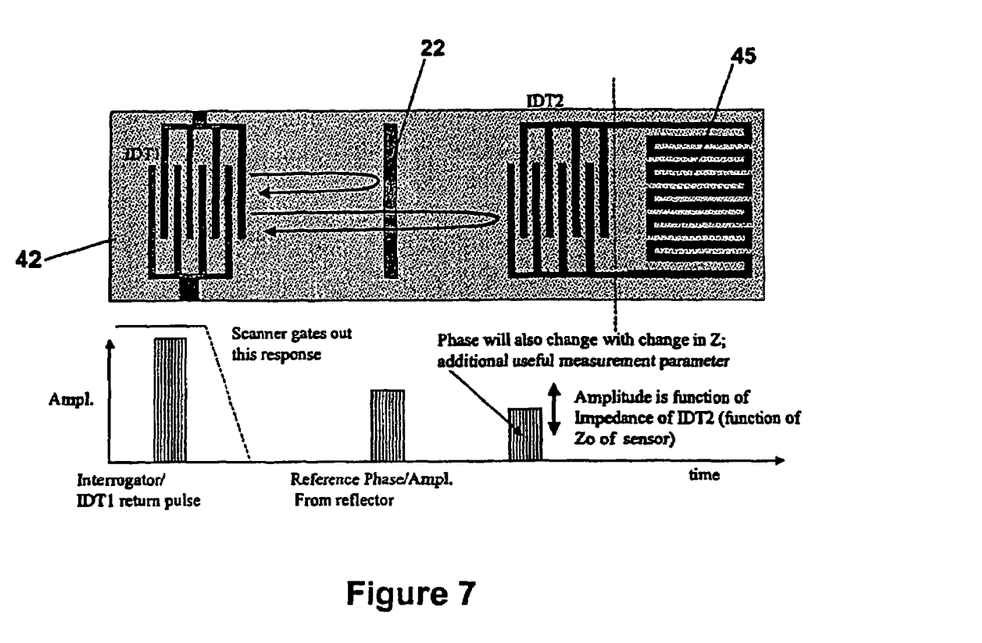
FIG. 7 provides a schematic diagram consistent with the diagram of FIG. 3 illustrating an integrated substrate including a SAW device and a meander line capacitor sensor.

FIGS. 4, 6 and 7 illustrate sensor configurations that operate so that the three constituent components of high frequency transmission lines, resistance (R (Z)), inductance (L), and capacitance (C) can be combined or separated out as seen fit. Such sensor types are described more completely in Kain I.

Figure 5:
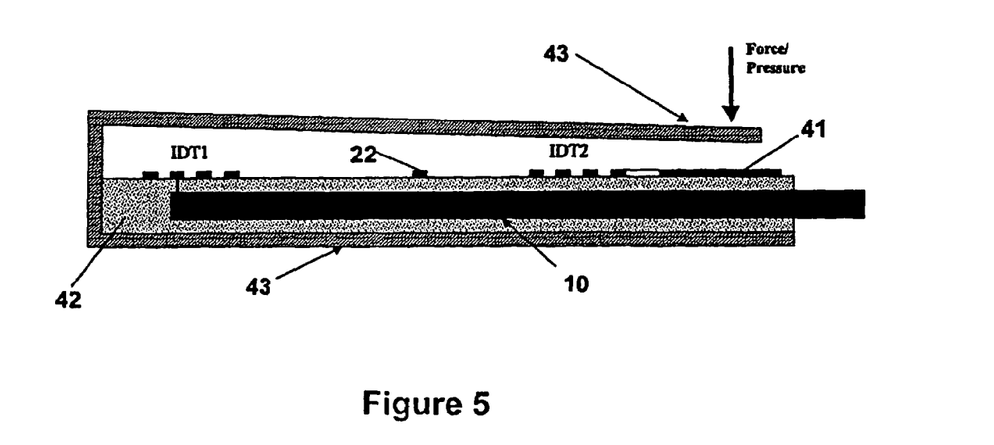
FIG. 5 illustrates the relationship between a deflecting member and sensor for the substrates of FIGS. 4, 6 and 7.

As illustrated in each of the sensor configurations of FIGS. 4, 6 and 7, the received signal will be a function of either change in amplitude or phase from the reference reflector. It is to be noted that the general effect of the deflecting member and how it effects the interdigital capacitance as shown in FIGS. 4 and 5, equally effects the inductance of coil 44 as illustrated in FIG. 6, and the impedance of meander line 45 as illustrated in FIG. 7. The key is, as is taught in Kain II, that by bringing a conductive material within the effected environment of either capacitive, inductive, or distributive elements (for example, meander line and transmission line elements), elements will effect the constituent characteristics (R, L and C) of that element because the EM fields of the element will be perturbed by the conductive deflecting spring member 43.

Figure 8:
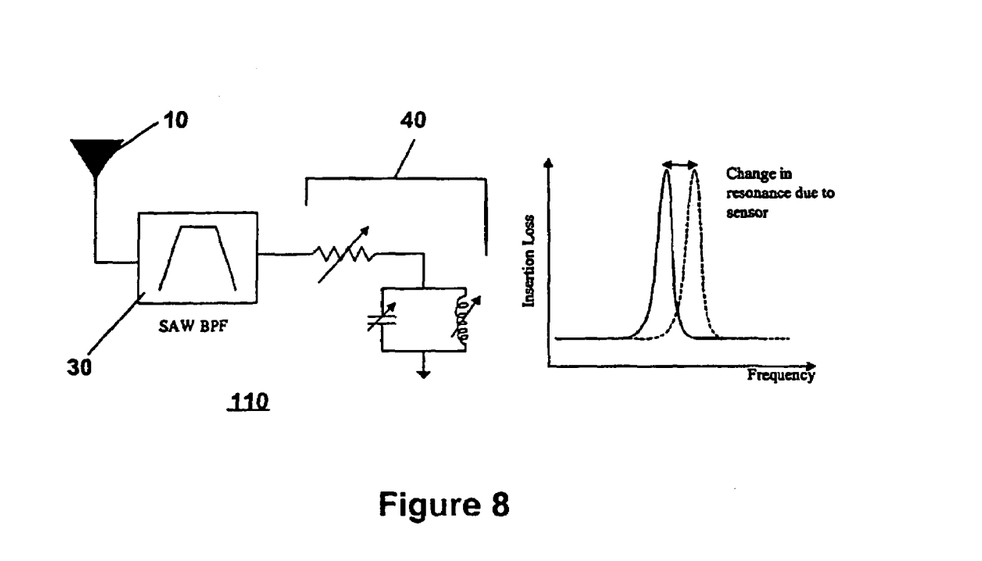
FIG. 8 provides a schematic diagram of an intra-corporeal transducer employing a SAW band pass fitter (BPF)

As illustrated in FIG. 8, a transducer 110 employing a SAW band pass filter (BPF) 30 may be used as an alternative to the SAW delay line. In this configuration, the sensor design functions as a time delayed frequency sensitive device, rather than as an amplitude and phase sensitive as in the case of the SAW delay line.

Figure 8A:
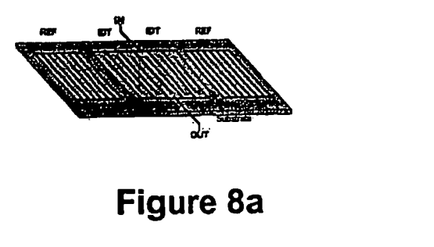
FIGS. 8a, 8b, and 8c illustrate several embodiments of SAW band pass filters.
Figure 8B:
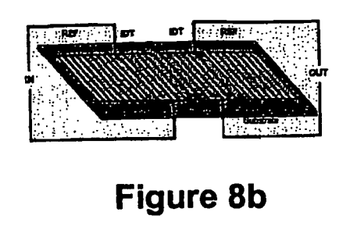
Figure 8C:
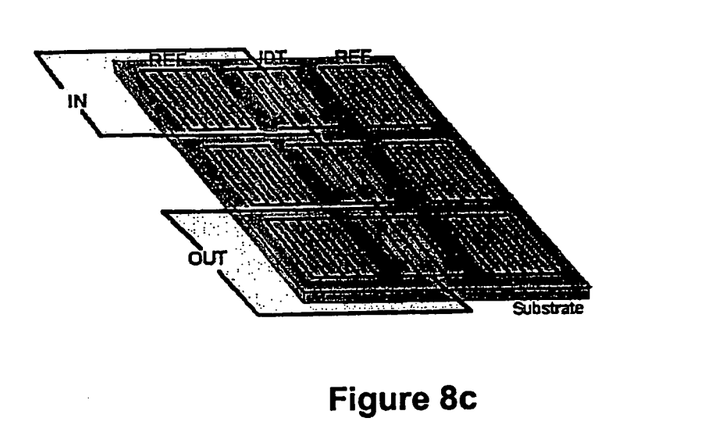

The SAW band pass filter 30 may be constructed by connecting individual SAW resonators in the usual filter design configuration such as ladder filters. Examples of typical SAW resonators are shown in FIGS. 8a–8c, including one-port resonator (FIG. 8a), two-port resonator (FIG. 8b) and ladder filter (FIG. 8c). The resonance components illustrated in FIGS. 8a–8c can used with any of the various sensors disclosed in Kain 1.

Figure 9:
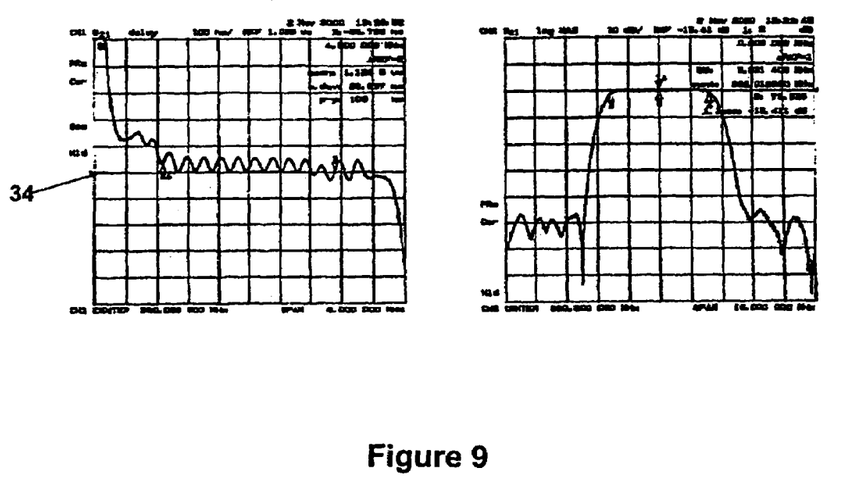
FIG. 9 illustrates performance characteristics of SAW band pass filters.

The SAW band pass filter (BPF) 30 has typical characteristics as shown in FIG. 9. Notice that even though the BPF has classic performance characteristics, that of passing a range of frequencies unperturbed, the SAW filter has the unique characteristic that the signal has an absolute group delay 34 (as seen in the left hand figure in FIG. 9, and given as 1.12 µs), which may generate the same delay effect as the SAW delay line 20 of FIG. 3. SAW BPF are typically more readily available and less expensive than SAW delay lines. Preferably, the SAW BPF 30 and sensor 40 are integrated within a single substrate, as illustrated for the transducers of FIGS. 4–7.

Although this disclosure focuses on SAW devices, due to their very slow propogation velocity, other types of delay lines may be employed, provided they exhibit adequate time delay. Such up and coming "slow wave" structures such as elevated Co-Planar Waveguide (CPW), Photonic Band Gap enhanced transmission lines, ferroelectric transmission lines, as well as nonlinear transmission lines are all possible alternative delay line structures. However, currently, the aforementioned "slow wave" structures currently fail to achieve the low propagation velocities achieved by mechanical/acoustical structures.

Measuring the blood pressure within a vein requires the measurement of pressures that are 10 mm Hg and below. As this is an exceptionally low value, special mechanical enhancements can be implemented in order to amplify the deflection of the member that ultimately causes the sensor to detect the pressure. An example of such a system is shown in FIG. 10.

Figure 10:
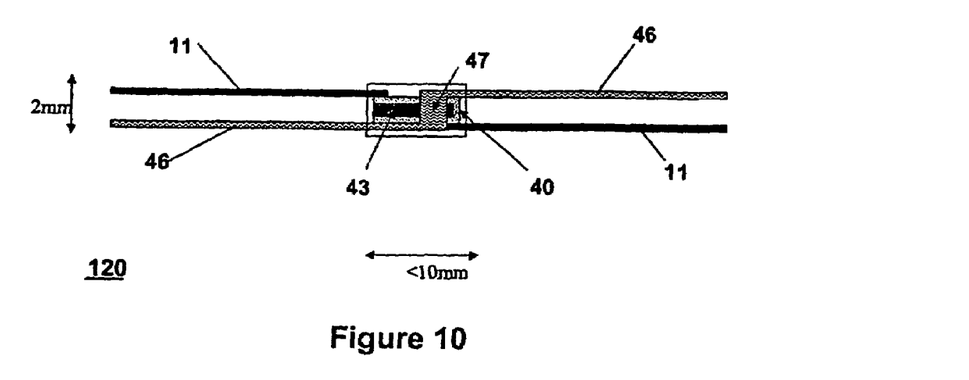
FIG. 10 shows a transducer for measuring venal blood pressure according to the principles of the present invention.
Figure 11:
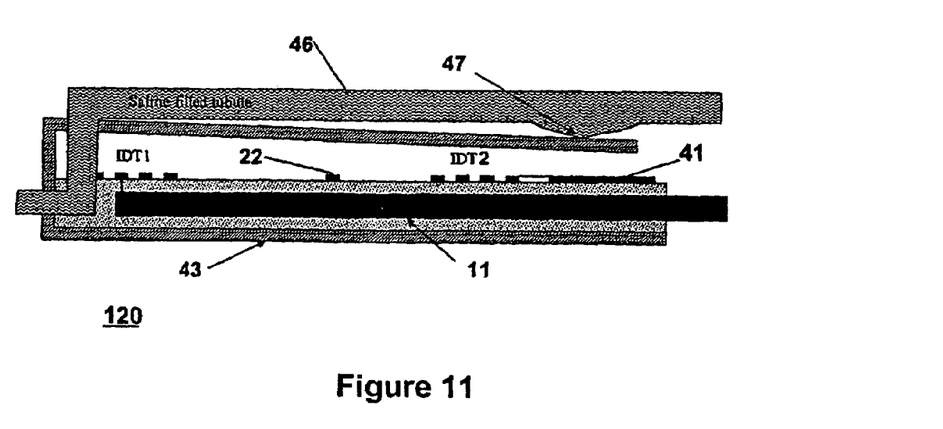
FIG. 11 presents a cross-sectional view of the transducer of FIG. 10.

The transducer 120 of FIG. 10 takes advantage of multilumen biocompatable tubing. Transducer 120 may fit, for example, within an overall inner tube diameter of 2 mm as shown in FIG. 10. A lumen 11 contains the NiTinol wire that acts as both the mechanical support when it coils within the vein and the electrical antenna that both transmits and receives the EM wave from the scanner 200 of FIG. 1. Another lumen 46 is sealed, and contains an incompressible fluid such as saline solution. The antenna 11 can either be a dipole antenna as shown or any other type of suitable antenna (for example, a ¼-wavelength whip). By using the well known hydraulic amplification principle, such as used in the design of car jacks and hoists, the nominal blood pressure exerts itself on the long length of the saline lumen 46. This results in a fractional change in volume of the saline lumen as it is squeezed. In order to maintain a constant pressure within the saline lumen 46, the deflecting diaphragm 47, which is more compliant than the saline lumen 46, must undergo a larger deflection which is then transmitted to deflecting spring member 43. Hence, small changes in the volume of saline lumen 46 will result in large deflections of diaphragm 47, and hence amplified mechanical to electrical sensor transduction. This is readily seen mathematically as:

$$Fd = Pd \times Ad = [Fl/Al] \times Ad \quad [1]$$

where the subscript d refers to the deflecting diaphragm 47 and l to the lumen 46. F is the force, P the pressure, and A the area of the respective lumen and diaphragm Since the saline volume V must remain constant because the fluid is incompressible, then $$Vl = Vd \quad [2]$$

so that $$Al \times Dl = Ad \times Dd \quad [3]$$

where D is the deflection of the saline lumen or the diaphragm. Hence the deflection of the diaphragm can be adjusted by simply optimizing the length of the saline tube knowing the applied deflection due to the applied blood pressure. FIG. 11 presents a cross-sectional view of the transducer 120. The diaphragm 47 should be suitably able to be deflected by the applied pressure to the lumen.

Figures 12, 13:
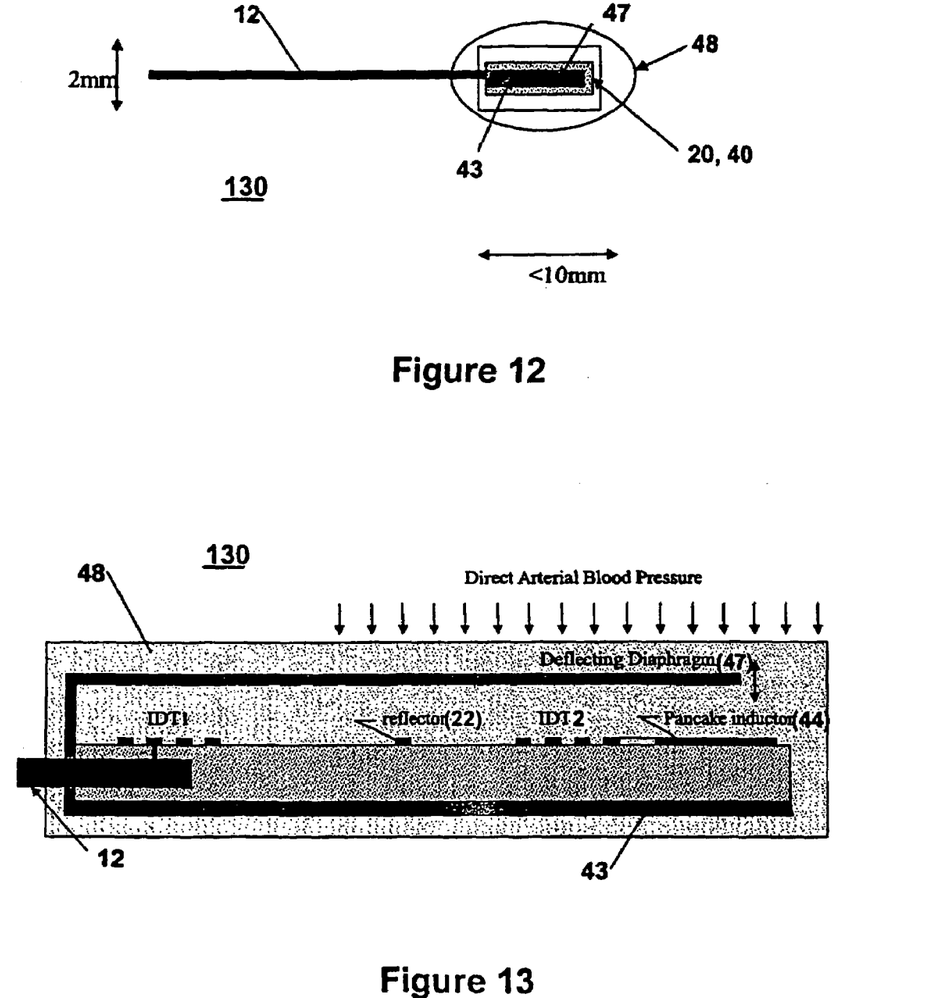
FIG. 12 shows a transducer for measuring arterial blood pressure according to the principles of the present invention.
FIG. 13 presents a cross-sectional view of the transducer of FIG. 12.

Measuring the blood pressure within an artery is significantly easier than measuring blood pressure in a vein, as the pressures generated are much greater. Therefore, although the same principles can be used as in the venal sensor of FIGS. 10 and 11, these are not necessarily required. FIG. 12 presents a schematic view of the arterial sensor, and FIG. 13 provides a cross-sectional view of the transducer 130 illustrated by FIG. 12.

Figure 14:
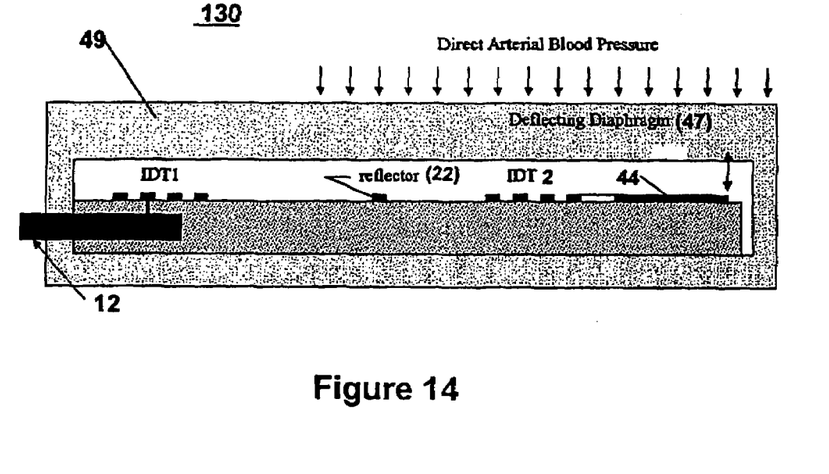
FIG. 14 illustrates an alternate transducer for the sensor of FIG. 12.

For transducer 130, the arterial blood pressure is large enough to directly cause the deflection of the folded cantilever 43 through the compliant urethane encapsulant 48. Alternatively, the folded cantilever beam 43 can be replaced by an encapsulant 49 including an embedded conductive silicone, such as that made for EMI gasketing (for example, by Rogers Corporation of Elk Grove Village, Ill.) and as shown in FIG. 14. The configuration of FIG. 14 eliminates the need for a separate mechanical bending member such as the folded cantilever beam 43.

It is important to note that, because the substrate 42 of the transducer 130 of FIGS. 12 and 13 is relatively thick and the pressures sensed are relatively low, the pressure does not directly effect the propagation characteristics of the SAW device. However, if the substrate is made thin enough so that the pressure does mechanically bend or distort it, of course, the propagation characteristics of the SAW device will be effected as well. Using thinned piezoelectric substrates for this effect is ell known in the art, and is contemplated as a means for altering the electrical and delay characteristics of the SAW device for the purposes of practicing the presently disclosed invention.

Figure 14A:
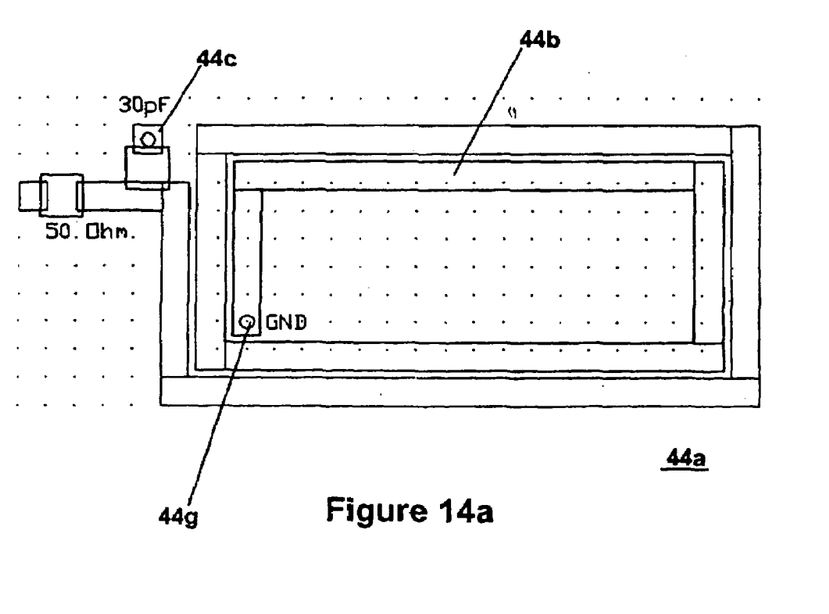
FIG. 14a illustrates a typical layout of an inductive sensor of the transducer of FIG. 12.
Figure 15:
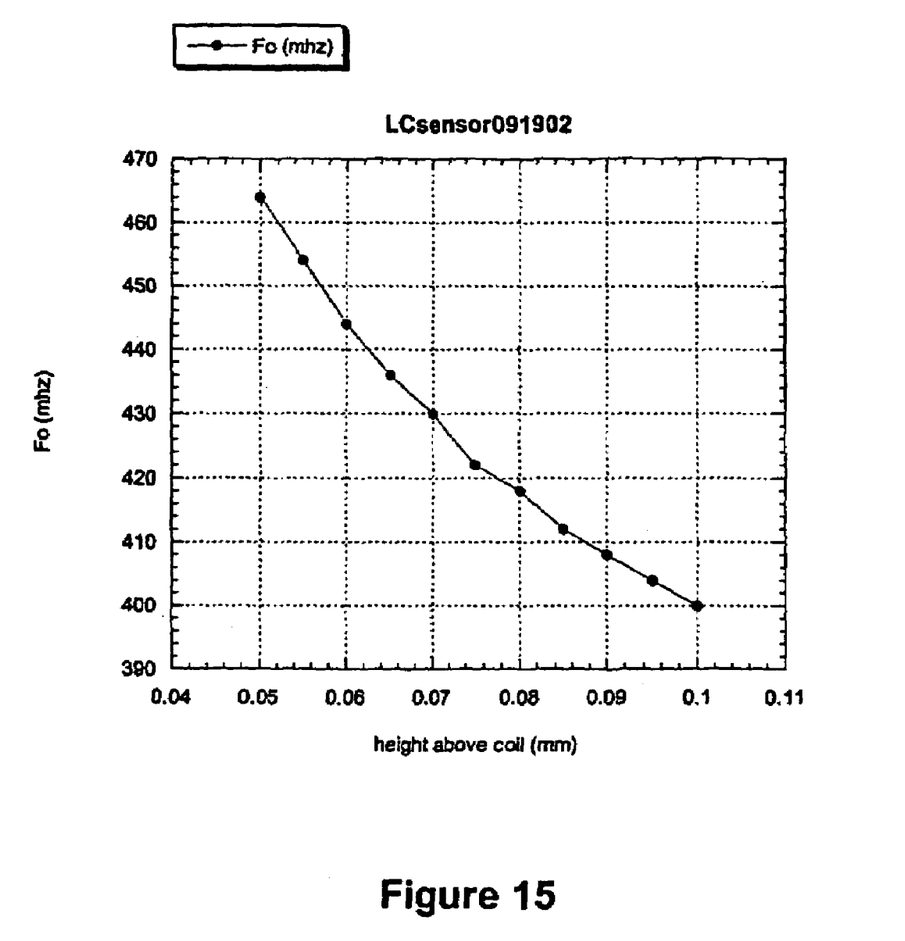

FIG. 14a illustrates a typical layout of an inductive sensor portion of the transducer 100 of FIG. 1. The entire sensor may be contained in an area 1 mm by 2 mm, and is arranged in a parallel LC arrangement as shown in FIG. 8, including inductor 44b and capacitor 44c. The illustrated chip capacitor 44c is readily available (for example, from American Technical Ceramics of Huntington Station, N.Y.). The curled line of inductor 44b terminates with ground pin 44g located at its serpentined end. As folded spring member 43 of FIG. 13 is brought close to inductor 44b, the inductance changes and hence the resonant response is shifted as shown in FIG. 8. A typical resonant frequency response as a function of conductor plate height above the inductor versus change in resonant frequency is shown in FIG. 15. The substrate is quartz and is assumed to be 0.005" thick, typical for SAW devices.

The foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A transducer for being remotely positioned in a fluid within a vessel and for sensing a pressure generated by the fluid in the vessel, the transducer comprising:
    an antenna for capturing an externally-generated interrogation signal and for transmitting a response signal;
    a response circuit coupled to the antenna for receiving the interrogation signal and for generating the response signal in response to the interrogation signal; and
    a sensor coupled to the response circuit for sensing the pressure generated by the fluid and adjusting one or more electrical characteristics of the response circuit in relation to the sensed pressure;
    wherein the response circuit causes a delay in the generation of the response signal so that the response signal is transmitted at a time separated from and following a transmission of artifacts of the interrogation signal.

2. The transducer of claim 1, wherein the response circuit comprises a surface acoustic wave (SAW) delay line.

3. The transducer of claim 1, wherein the response circuit comprises a surface acoustic wave (SAW) bandpass filter.

4. The transducer of claim 1, wherein the transducer further includes means for attachment to an inner wall of the vessel.

5. The transducer of claim 4, wherein the antenna comprises a shape memory alloy.

6. The transducer of claim 5, wherein the antenna is insertable into the vessel, and changes shape become affixed to an inner wall of the vessel in response to a characteristic of the fluid.

7. The transducer of claim 5, wherein the shape memory alloy is formed as a wire and enclosed within a lumen.

8. The transducer of claim 5, wherein the shape memory alloy is NiTinol.

9. The transducer of claim 2, wherein the SAW delay line includes:
    a first interdigital transducer (IDT) coupled to the antenna for receiving the interrogation signal and generating a first SAW; and
    a second IDT positioned at a distance L2 from the first IDT, the second IDT coupled to the sensor for receiving the first SAW and transmitting a response SAW to the first IDT;
    wherein the first IDT generates the response signal from the response SAW, the antenna transmits the response signal, and signal characteristics of the response signal indicate a property of the fluid.

10. The transducer of claim 9, wherein the SAW delay line further includes:
    a reflector positioned at a distance L1 from the first IDT, the reflector for receiving the first SAW and reflecting a reference SAW to the first IDT;
    wherein the first IDT generates a reference signal from the reference SAW, the antenna transmits the reference signal, and signal characteristics of the reference signal as compared to signal characteristics of the response signal indicate a property of the fluid.

11. The transducer of claim 9, wherein the signal characteristics include at least one of signal amplitude and signal phase.

12. The transducer of claim 2, wherein one or more electrical characteristics of the response circuit include at least one of resistance, inductance and capacitance.

13. The transducer of claim 3, wherein one or more characteristics of the response signal associated with a resonant frequency of the response circuit may be used to determine a property of the fluid.

14. The transducer of claim 1, wherein the transducer further comprises a deflecting spring member movable in proximity to the sensor in response to the pressure generated by the fluid, wherein a position of the deflecting spring relative to the sensor determines the one or more electrical characteristics of the response circuit.

15. The transducer of claim 14, wherein the deflecting spring member comprises a conductive encapsulant movable in proximity to the sensor.

16. The transducer of claim 15, wherein the conductive encapsulant comprises a conductive silicone.

17. The transducer of claim 14, further comprising amplification means coupled to the deflecting spring member for generating the pressure to be sensed.

18. The transducer of claim 17, wherein the amplification means comprises:
   a lumen containing an incompressible fluid in a sealed lumen tube, a portion of the lumen tube having deflecting diaphragm coupled to the deflecting spring member, wherein the deflecting diaphragm is more compliant and undergoes a larger deflection than the lumen tube in response to a generated pressure.

19. The transducer of claim 18, wherein the ratio of a deflection of the diaphragm to the deflection of the lumen tube in response to the generated pressure is inversely proportional to the ratio of a surface area of the tube to a surface area of the diaphragm.

20. The transducer of claim 1, wherein the artifacts include at least one of one of more reflections of the interrogation signal and one or more undesired replies to the interrogation signal.

21. The transducer of claim 1, wherein the response circuit causes a delay following the interrogation signal of a predetermined period.

22. The transducer of claim 21, wherein the predetermined period is approximately 2 microseconds.

23. A system for remotely sensing a pressure generated by a fluid within a vessel, comprising:
   a scanner for generating an interrogation signal and receiving a response signal, the scanned being positioned externally with respectect to the vessel; and
   a transducer positioned within the vessel, the transducer including:
   an antenna for receiving the interrogation signal and for transmitting the response signal;
   a response circuit coupled to the antenna for receiving the interrogation signal and generating the response signal in response to the interrogation signal; and
   a sensor coupled to the response circuit for sensing the pressure generated by the fluid and adjusting one or more electrical characteristics of the response circuit in relation to the sensed pressure;
   wherein the response circuit causes a delay in the transmission of the response signal so that the response signal is transmitted at a time separated from and following transmission of artifacts of the interrogation signal.

* * * * *